US00PP29978P3

(12) United States Plant Patent
Koot

(10) Patent No.: US PP29,978 P3
(45) Date of Patent: Dec. 11, 2018

(54) ***PETUNIA* PLANT NAMED 'DUEFORTELECBLU'**

(50) Latin Name: *Petunia X hybrida*
Varietal Denomination: Duefortelecblu

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 117 days.

(21) Appl. No.: 15/530,744

(22) Filed: Feb. 22, 2017

(65) Prior Publication Data

US 2018/0242496 P1 Aug. 23, 2018

(51) Int. Cl.
*A01H 5/02* (2018.01)

(52) U.S. Cl.
USPC ..... Plt./356.2

(58) Field of Classification Search
USPC ..... Plt./356.2
See application file for complete search history.

*Primary Examiner* — Annette H Para
(74) *Attorney, Agent, or Firm* — C. A. Whealy

(57) ABSTRACT

A new and distinct cultivar of *Petunia* plant named 'Duefortelecblu', characterized by its medium to compact plant size; mounding to trailing plant habit; moderately vigorous growth habit; freely branching habit; early and freely flowering habit; flowers with light and dark violet bi-colored petals and dark purple-colored throats; and good garden performance.

1 Drawing Sheet

Botanical designation: *Petunia* X *hybrida.*
Cultivar denomination: 'DUEFORTELECBLU'.

BACKGROUND OF THE INVENTION

The present invention relates to a new and distinct cultivar of *Petunia* plant, botanically known as *Petunia* X *hybrida* and hereinafter referred to by the name 'Duefortelecblu'.

The new *Petunia* plant is a product of a planned breeding program conducted by the Inventor in Rheinberg, Germany. The objective of the breeding program is to create new moderately vigorous and early-flowering *Petunia* plants with numerous attractive bi-colored flowers.

The new *Petunia* plant originated from a cross-pollination made by the Inventor in July, 2014 in Rheinberg, Germany of a proprietary selection of *Petunia* X *hybrida* identified as code number TT13-002630-001, not patented, as the female, or seed, parent with a proprietary selection of *Petunia* X *hybrida* identified as code number TT13-003335-002, not patented, as the male, or pollen, parent. The new *Petunia* plant was discovered and selected by the Inventor as a single flowering plant from within the progeny of the stated cross-pollination in a controlled greenhouse environment in Rheinberg, Germany in May, 2016.

Asexual reproduction of the new *Petunia* plant by terminal cuttings in a controlled greenhouse environment in Rheinberg, Germany since June, 2016 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duefortelecblu'. These characteristics in combination distinguish 'Duefortelecblu' as a new and distinct *Petunia* plant:

1. Medium to compact plant size, mounding to trailing plant habit.
2. Moderately vigorous growth habit.
3. Freely branching habit.
4. Early and freely flowering habit.
5. Flowers with light and dark violet bi-colored petals with dark purple-colored throats.
6. Good garden performance.

Plants of the new *Petunia* can be compared to plants of the female parent selection. Plants of the new *Petunia* differ primarily from plants of the female parent selection in plant size as plants of the new *Petunia* are not as compact as plants of the female parent selection. In addition, plants of the new *Petunia* and the female parent selection differ in flower color as plants of the female parent selection have purple-colored flowers.

Plants of the new *Petunia* can be compared to plants of the male parent selection. Plants of the new *Petunia* differ primarily from plants of the male parent selection in plant size as plants of the new *Petunia* are more compact than and not as vigorous as plants of the male parent selection. In addition, plants of the new *Petunia* and the male parent selection differ in flower color as plants of the male parent selection have blue-colored flowers.

Plants of the new *Petunia* can be compared to plants of *Petunia* X *hybrida* 'Sunsurfbv', disclosed in U.S. Plant Pat. No. 17,735. Plants of the new *Petunia* and 'Sunsurfbv' differ primarily in the following characteristics:

1. Plants of the new *Petunia* are more compact and have shorter internodes than plants of 'Sunsurfbv'.

2. Plants of the new *Petunia* have narrower leaves than plants of 'Sunsurfbv'.
3. Plants of the new *Petunia* flower earlier than plants of 'Sunsurfbv'.
4. Plants of the new *Petunia* and 'Sunsurfbv' differ in flower color as plants of 'Sunsurfbv' have light lavender-colored flowers with purple-colored venation.

BRIEF DESCRIPTION OF THE PHOTOGRAPH

The accompanying colored photograph illustrates the overall appearance of the new *Petunia* plant showing the colors as true as it is reasonably possible to obtain in colored reproductions of this type. Colors in the photograph may differ slightly from the color values cited in the detailed botanical description which accurately describe the colors of the new *Petunia* plant.

The photograph is a side perspective view of a typical flowering plant of 'Duefortelecblu'.

DETAILED BOTANICAL DESCRIPTION

The aforementioned photograph and following observations, measurements and values describe plants grown during the summer in 22-cm containers in a glass-covered greenhouse in Rheinberg, Germany and under cultural practices typical of commercial *Petunia* production. During the production of the plants, day and night temperatures averaged 18° C. and light levels averaged 4,500 lux. Plants were 13 weeks old when the photograph and description were taken. In the following description, color references are made to The Royal Horticultural Society Colour Chart, 2007 Edition, except where general terms of ordinary dictionary significance are used.

Botanical classification: *Petunia* X *hybrida* 'Duefortelecblu'.

Parentage:

*Female, or seed, parent*.—Proprietary selection of *Petunia* X *hybrida* identified as code number TT13-002630-001, not patented.

*Male, or pollen, parent*.—Proprietary selection of *Petunia* X *hybrida* identified as code number TT13-003335-002, not patented.

Propagation:

*Type*.—By terminal cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Medium to compact plant size, mounding to trailing plant habit; freely branching habit with about seven to nine lateral branches developing after pinching; moderately vigorous growth habit.

*Plant height*.—About 30 cm.

*Plant diameter*.—About 66 cm.

Lateral branch description:

*Length*.—About 65 cm.

*Diameter*.—About 5 mm.

*Internode length*.—About 2.8 cm.

*Strength*.—Moderately strong.

*Aspect*.—Initially upright to outwardly spreading.

*Texture*.—Pubescent.

*Color*.—Close to 144A.

Leaf description:

*Arrangement*.—Before flowering, alternate; after flowering, opposite; simple.

*Length*.—About 4.2 cm.

*Width*.—About 2.9 cm.

*Shape*.—Spatulate.

*Apex*.—Obtuse.

*Base*.—Attenuate.

*Margin*.—Entire.

*Texture, upper and lower surfaces*.—Pubescent; leathery.

*Venation pattern*.—Pinnate; arcuate.

*Color*.—Developing and fully expanded leaves, upper surface: Close to 146A; venation, close to 146A. Developing and fully expanded leaves, lower surface: Close to 146B; venation, close to 146B.

*Petioles*.—Length: About 4.2 mm. Diameter: About 2.4 mm. Texture, upper and lower surfaces: Pubescent. Color, upper and lower surfaces: Close to 144B.

Flower description:

*Flower type and flowering habit*.—Single salverform flowers arising from leaf axils; freely flowering habit with usually about nine to twelve open flowers and flower buds per lateral branch and about 63 to 108 flowers developing per plant; flowers face mostly upright to outwardly.

*Fragrance*.—None detected.

*Natural flowering season*.—Plants flower continuously during the spring and summer in Germany; early flowering habit, plants typically beginning flowering about nine weeks after planting.

*Flower longevity*.—Individual flowers last about five to six days on the plant; flowers persistent.

*Flower buds*.—Length: About 2.4 cm. Diameter: About 5 mm. Shape: Ovoid. Color: Close to 145C.

*Flower diameter*.—About 4.8 cm.

*Flower depth (height)*.—About 4.6 cm.

*Flower throat diameter*.—About 9 mm.

*Flower tube length*.—About 2.6 cm.

*Flower tube diameter*.—About 2 mm.

*Corolla*.—Arrangement: Five petals fused at the base and opening into a flared trumpet. Petal lobe length (from throat): About 1.9 cm. Petal lobe width: About 2.1 cm. Petal shape: Roughly spatulate. Petal apex: Obtuse. Petal margin: Entire. Petal texture, upper and lower surfaces: Rippled, glabrous. Throat texture: Rippled, glabrous. Tube texture: Rippled, pubescent. Color: Petal lobe, when opening, upper surface: Close to 85D; towards the throat, close to 86A. Petal lobe, when opening, lower surface: Close to 85D; towards the tube, close to 86B. Petal lobe, fully opened, upper surface: Close to 85D; towards the throat, close to 83B; venation, close to 83A; color becoming closer to 92C and towards the throat, close to 86B, with development. Petal lobe, fully opened, lower surface: Close to 85D; towards the tube, close to 83D; venation, close to 83C. Flower throat: Close to 79A; venation, close to N77A. Flower tube: Close to 79B; venation, close to 83C.

*Calyx*.—Arrangement: Five sepals fused at the base forming a star-shaped calyx. Sepal length: About 1.8 cm. Sepal width: About 3.7 mm. Sepal shape: Oblong. Sepal apex: Rounded. Sepal margin: Entire. Sepal texture, upper and lower surfaces: Smooth. Color, upper surface: Close to 147A. Color, lower surface: Close to 147B.

*Peduncles*.—Length: About 3.7 cm. Diameter: About 1.5 mm. Strength: Moderately strong. Texture: Smooth. Color: Close to 143C.

*Reproductive organs*.—Stamens: Quantity per flower: Five. Filament length: About 1.7 cm. Filament color: Close to 157D. Anther length: About 2 mm. Anther shape: Ovate. Anther color: Close to 90D. Pollen amount: Abundant. Pollen color: Close to 93D. Pistils: Quantity per flower: One. Pistil length: About 2.1 cm. Style length: About 1.9 cm. Style color: Close to 145C. Stigma shape: Rounded. Stigma color: Close to 137B. Ovary color: Close to N144C. Seeds and fruits: Seed and fruit development have not been observed on plants of the new *Petunia*.

Garden performance: Plants of the new *Petunia* have been observed to have good garden performance and tolerate wind, rain and temperatures ranging from about 5° C. to about 40° C.

Pathogen & pest resistance: Plants of the new *Petunia* have not been observed to be resistant to pathogens and pests common to *Petunia* plants.

It is claimed:

1. A new and distinct *Petunia* plant named 'Duefortelecblu' as illustrated and described.

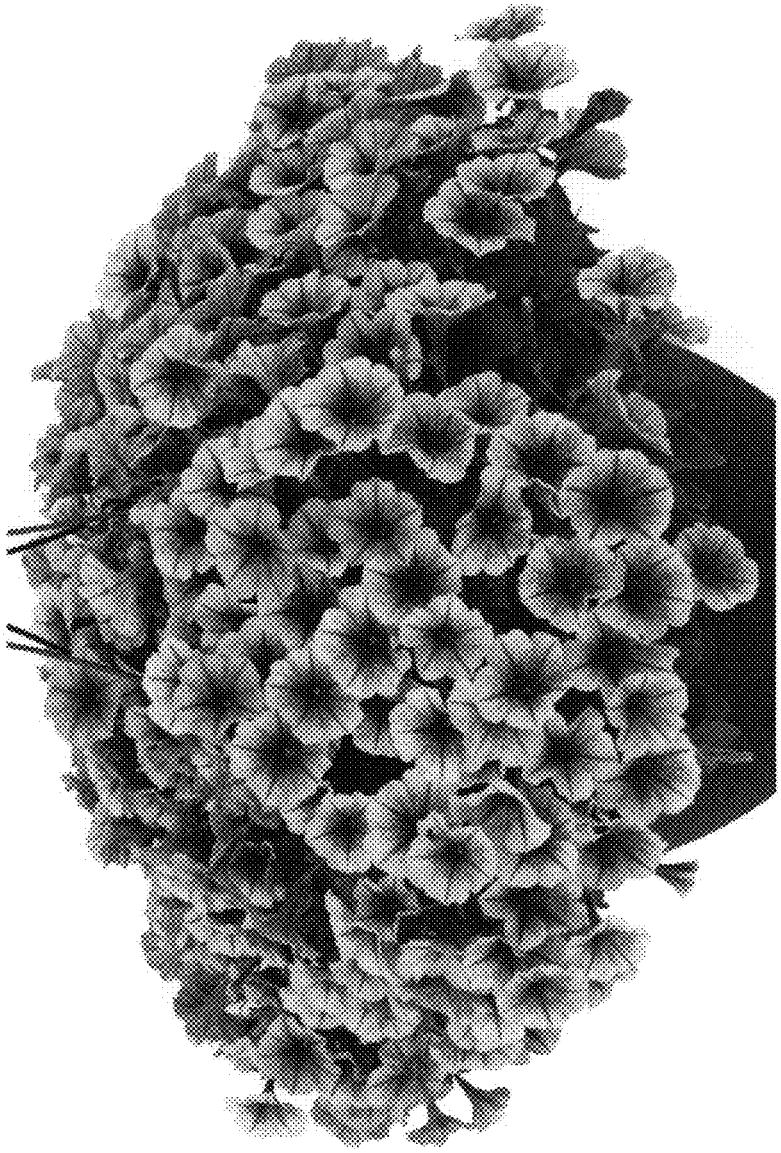

* * * * *